United States Patent [19]

Protzmann et al.

[11] 4,439,190

[45] Mar. 27, 1984

[54] UNDERWATER DRAINAGE DEVICE

[75] Inventors: Donald E. Protzmann, Litchfield; Ronald P. Roveda, Monroe, both of Conn.; John Uhoch, Warwich, R.I.

[73] Assignee: Chesebrough-Pond's Inc., Greenwich, Conn.

[21] Appl. No.: 257,953

[22] Filed: Apr. 27, 1981

[51] Int. Cl.³ .............................................. A61M 1/00
[52] U.S. Cl. .................................... 604/319; 137/205
[58] Field of Search ....................... 248/339, 341, 304; 128/276, 760, DIG. 2, 276; 220/293, 300; 215/332; 137/205, 593; 366/139; 604/317, 319, 320, 321; 181/233, 234, 235

[56] References Cited

U.S. PATENT DOCUMENTS

| | | | |
|---|---|---|---|
| 2,078,743 | 4/1937 | Traum | 220/293 |
| 2,194,163 | 3/1940 | Dahl | 181/233 |
| 2,438,245 | 3/1948 | Gregg | 137/592 X |
| 3,220,434 | 11/1965 | Garth | 128/DIG. 24 |
| 3,279,467 | 10/1966 | Hofstra et al. | 128/276 |
| 3,363,626 | 1/1968 | Bidwell et al. | 128/276 |
| 3,750,692 | 8/1973 | Tibbs | 128/276 |
| 3,782,497 | 1/1974 | Bidwell et al. | 181/233 |
| 3,855,997 | 12/1974 | Sauer | 215/332 |
| 4,018,224 | 4/1977 | Kurtz et al. | 128/276 |
| 4,258,824 | 3/1981 | Kurtz et al. | 181/233 |
| 4,261,362 | 4/1981 | Kurtz et al. | 128/276 |
| 4,270,539 | 6/1981 | Frosch et al. | 128/295 |
| 4,289,158 | 9/1981 | Nehring | 128/276 |
| 4,324,244 | 4/1982 | Kurtz et al. | 128/276 |
| 4,372,336 | 2/1983 | Cornell et al. | 604/319 |

*Primary Examiner*—C. Fred Rosenbaum
*Assistant Examiner*—J. L. Kruter
*Attorney, Agent, or Firm*—Morgan, Finnegan, Pine, Foley & Lee

[57] ABSTRACT

An underwater drainage device for removing fluid, blood and gases from the pleural cavity between the lung and the surrounding rib cage of patient. The underwater drainage device includes a collection chamber in fluid communication with the patient, a water seal chamber and a suction chamber. There is a baffled manifold which interconnects and provides fluid communication between the chambers. The collection chamber is removably connected to the manifold to permit emptying and/or testing of the fluid therein. The manometer chamber is also removable to permit changing the amount of suction. There is an anti-flux device which retards liquid flow from the water seal chamber in the event of high negativity at the patient. The device is constructed so that there is minimal fluid loss in the event the device is knocked over and there is a stand and hooks for positioning the underwater drainage device where desired.

28 Claims, 28 Drawing Figures

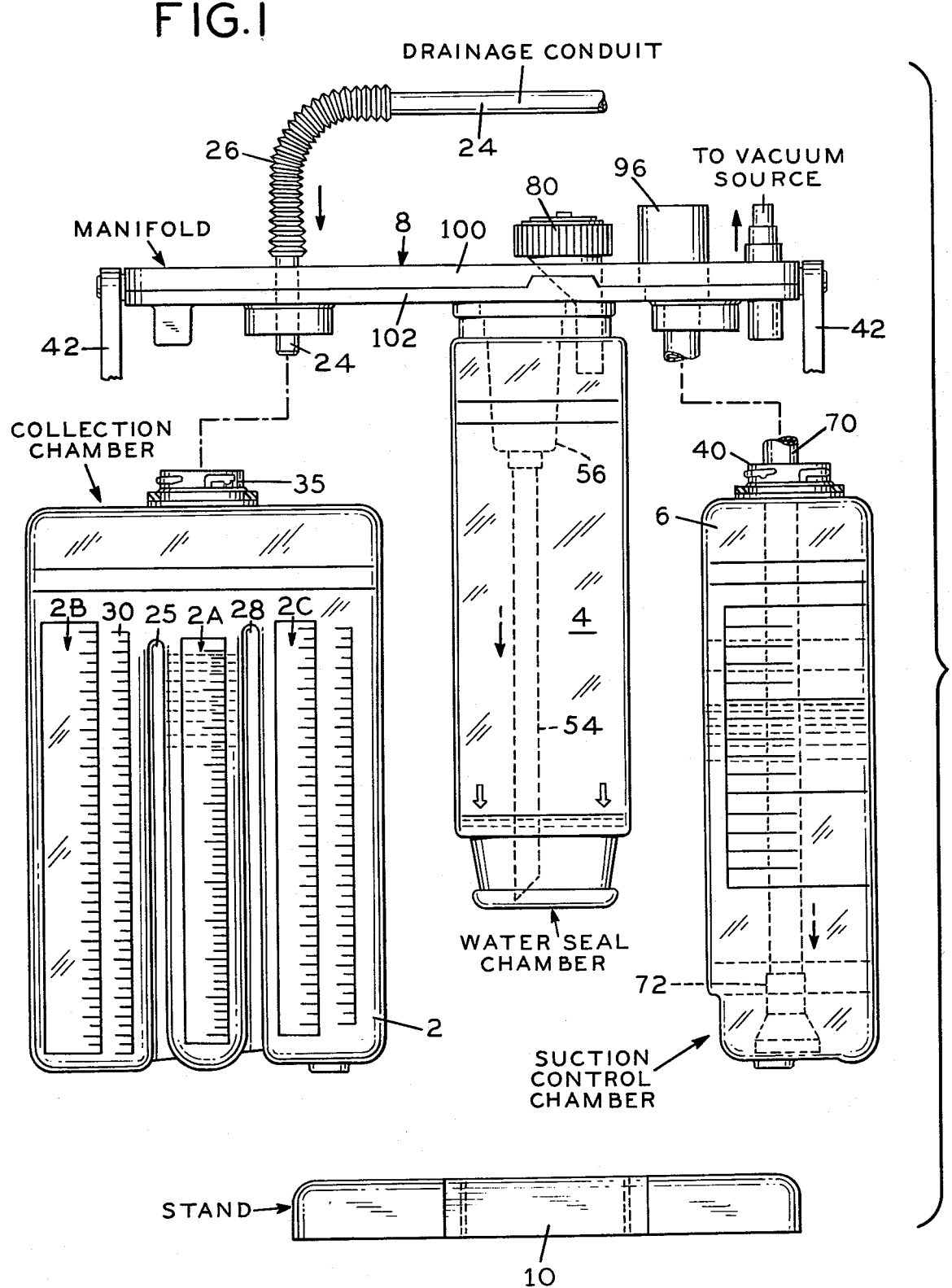

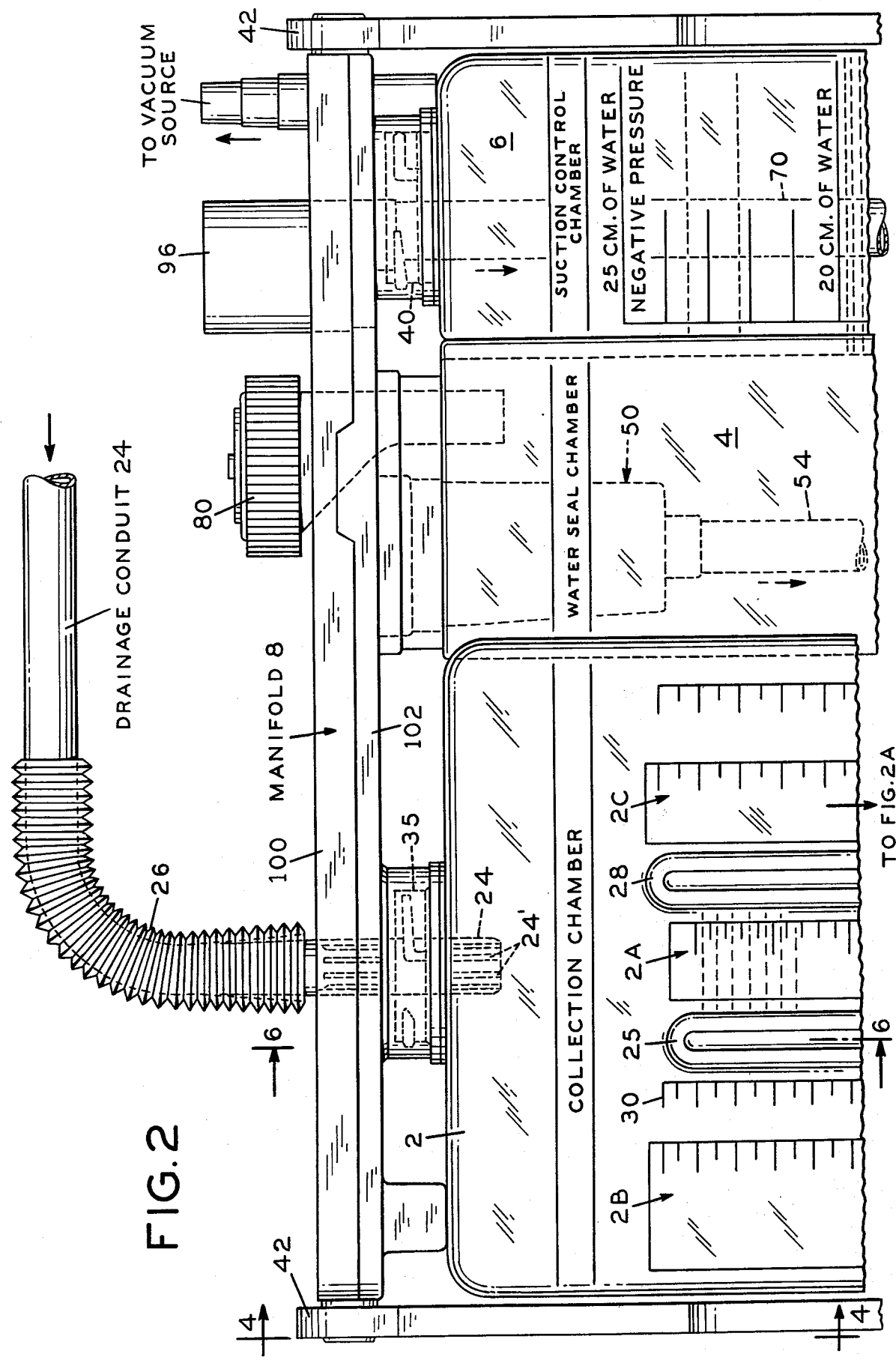

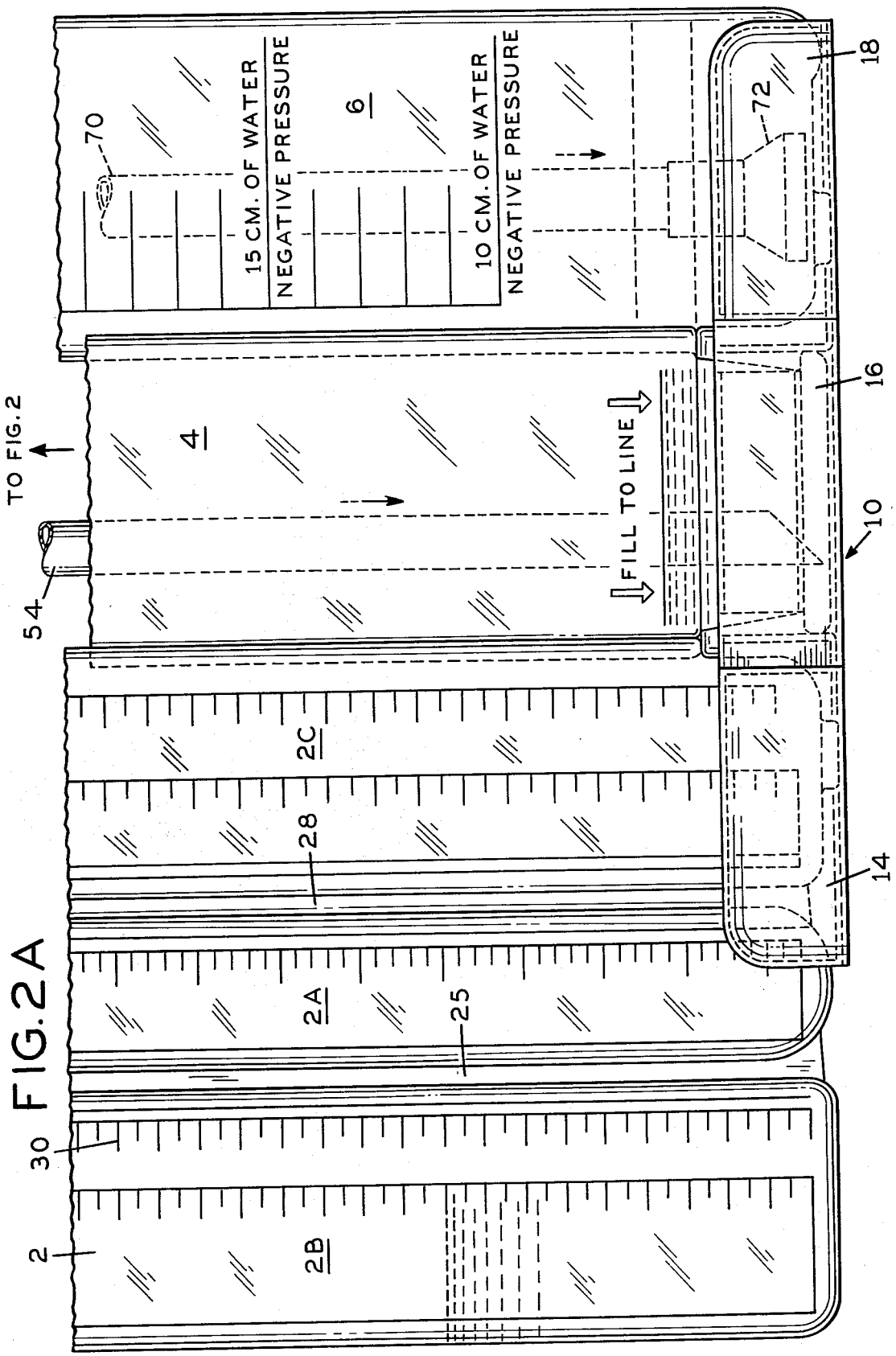

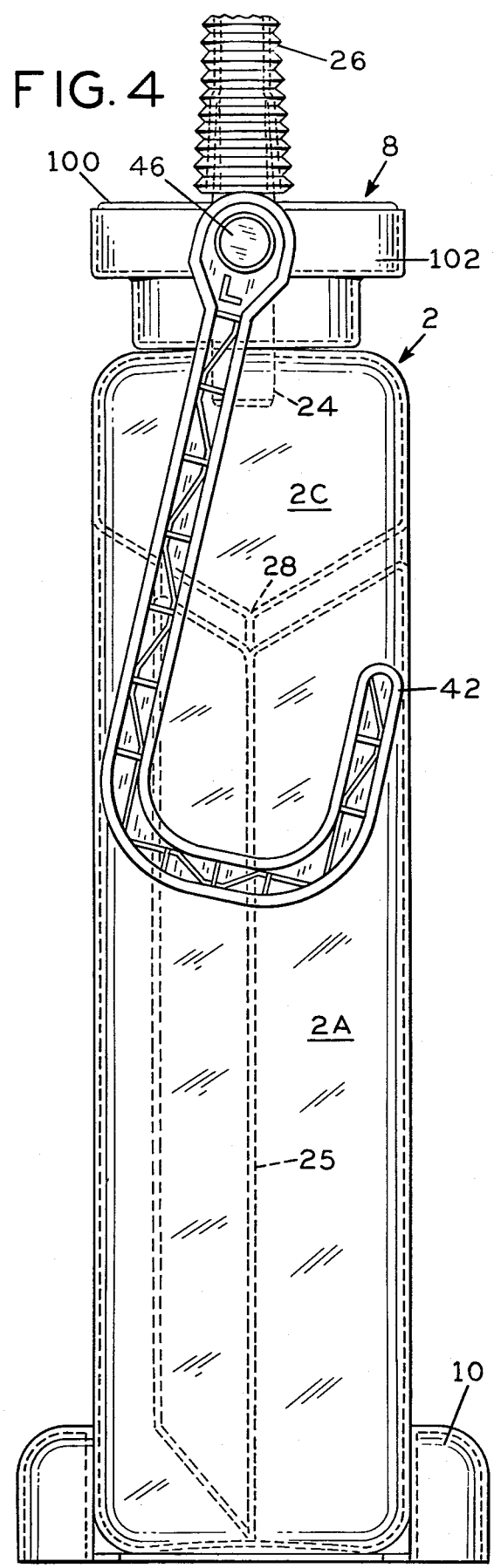
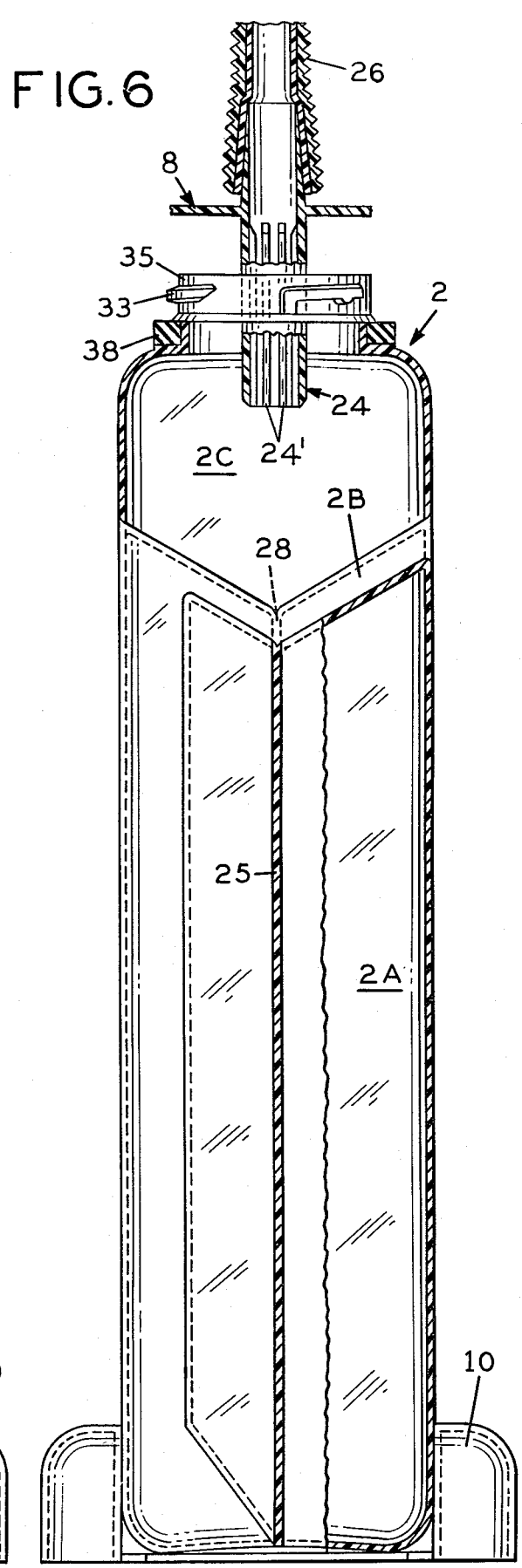

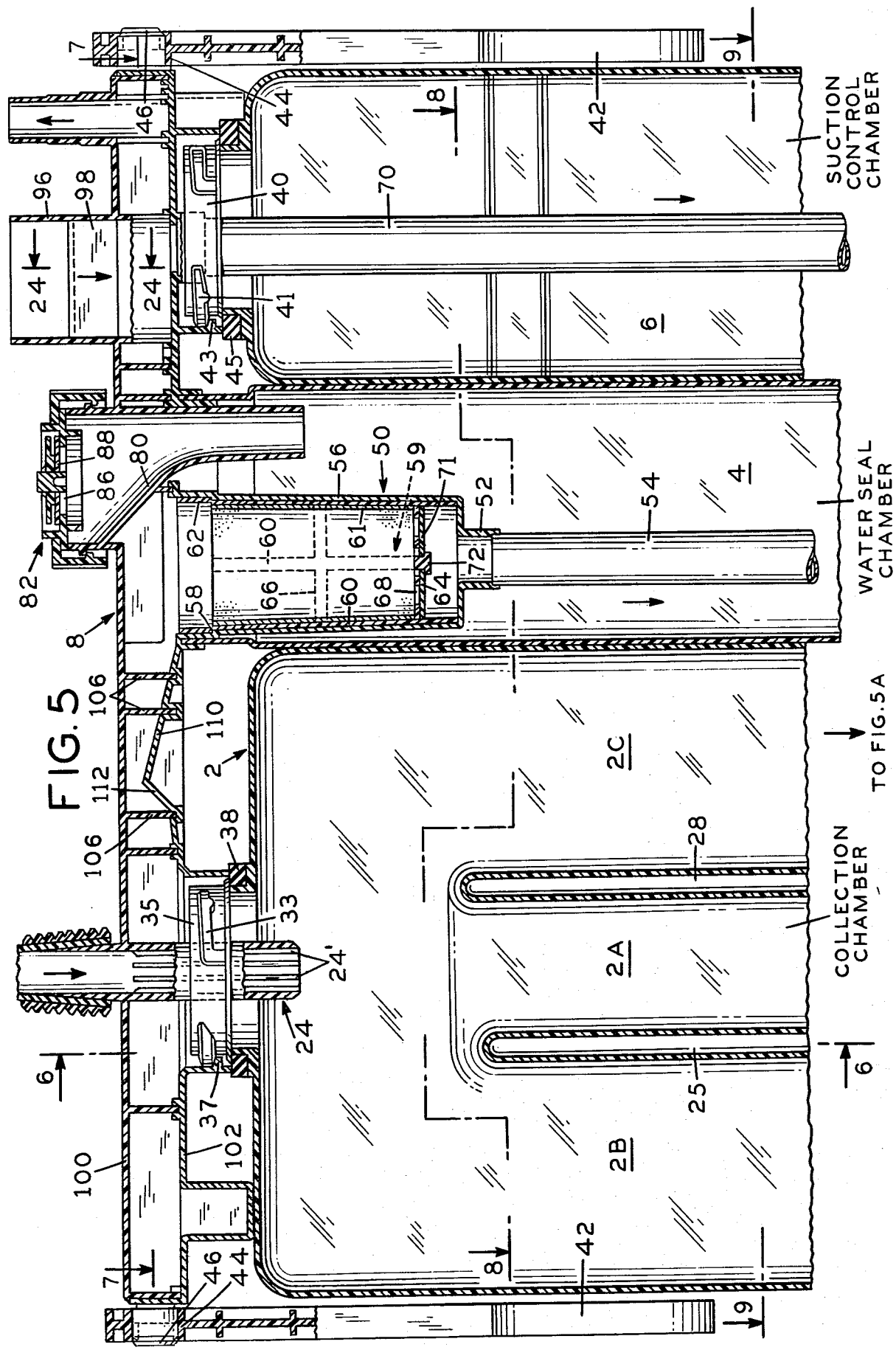

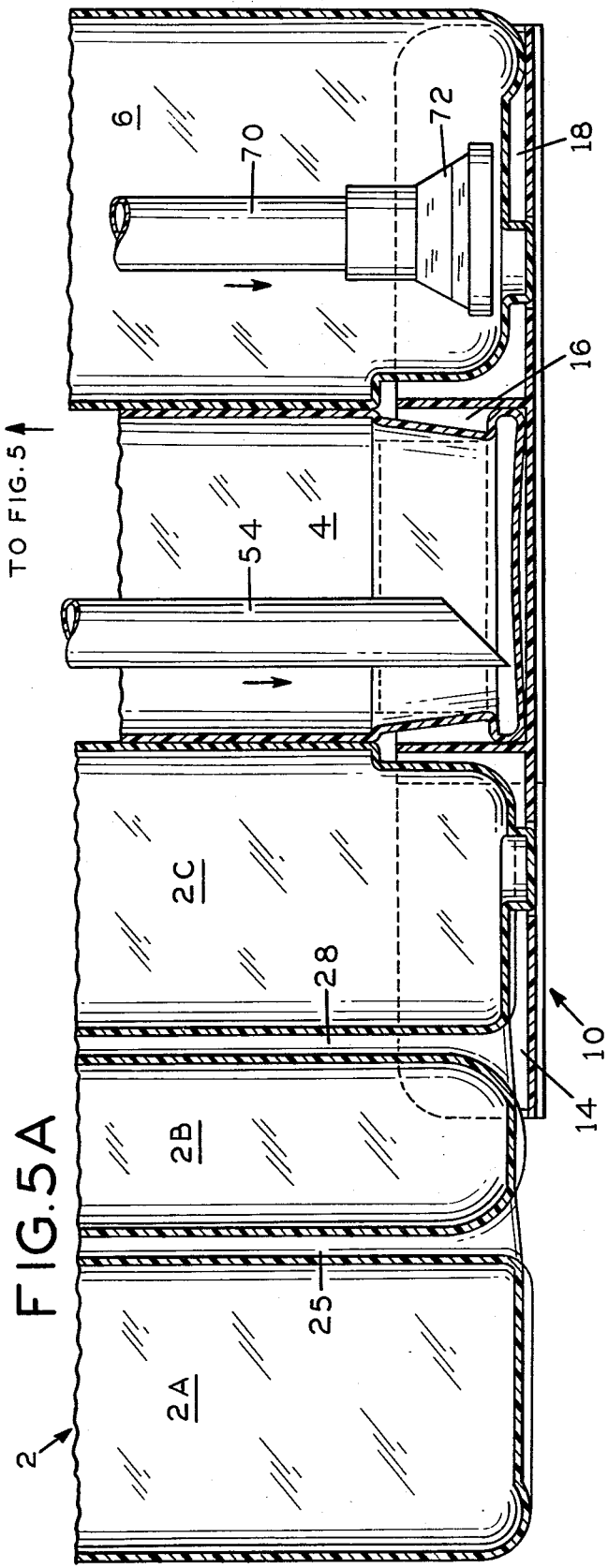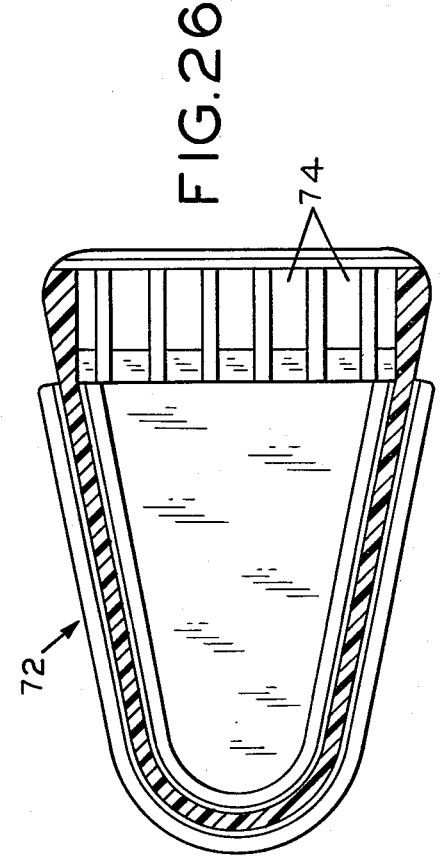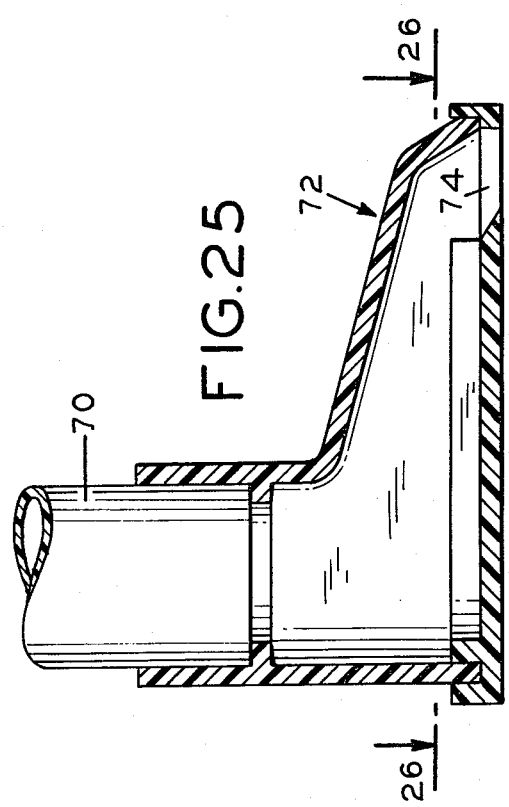

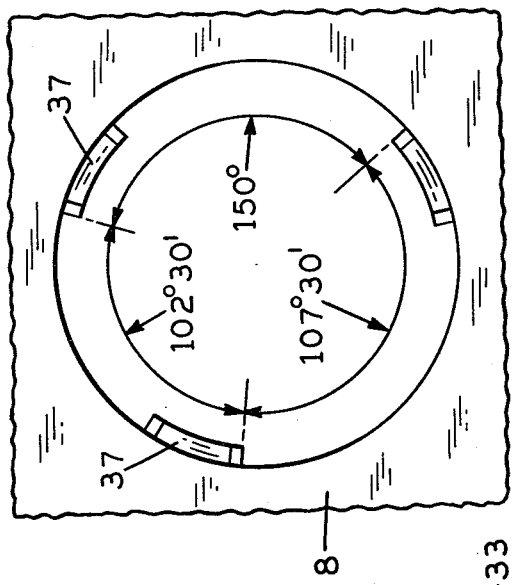
FIG.15
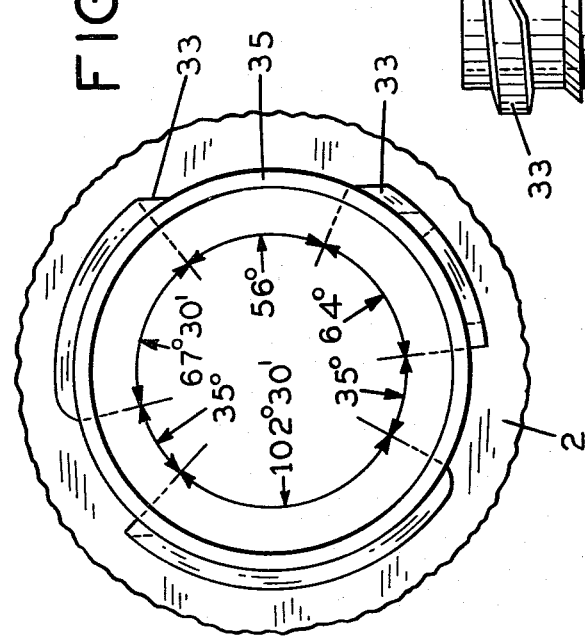
FIG.13
FIG.12
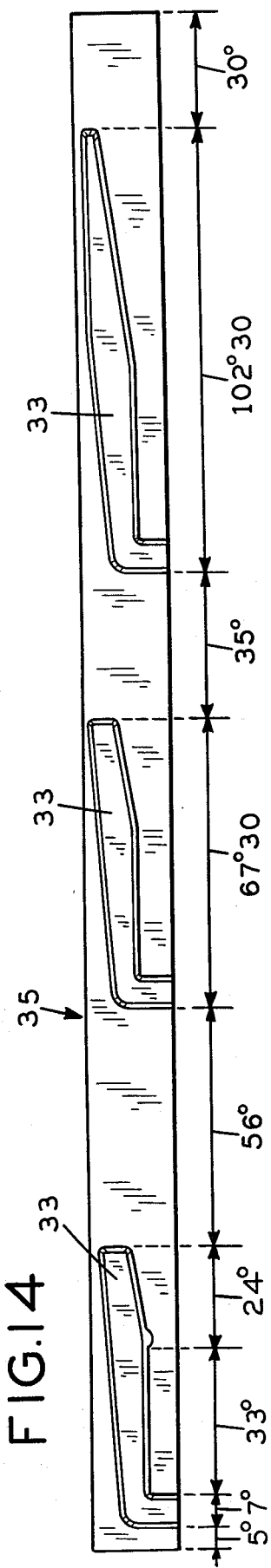
FIG.14

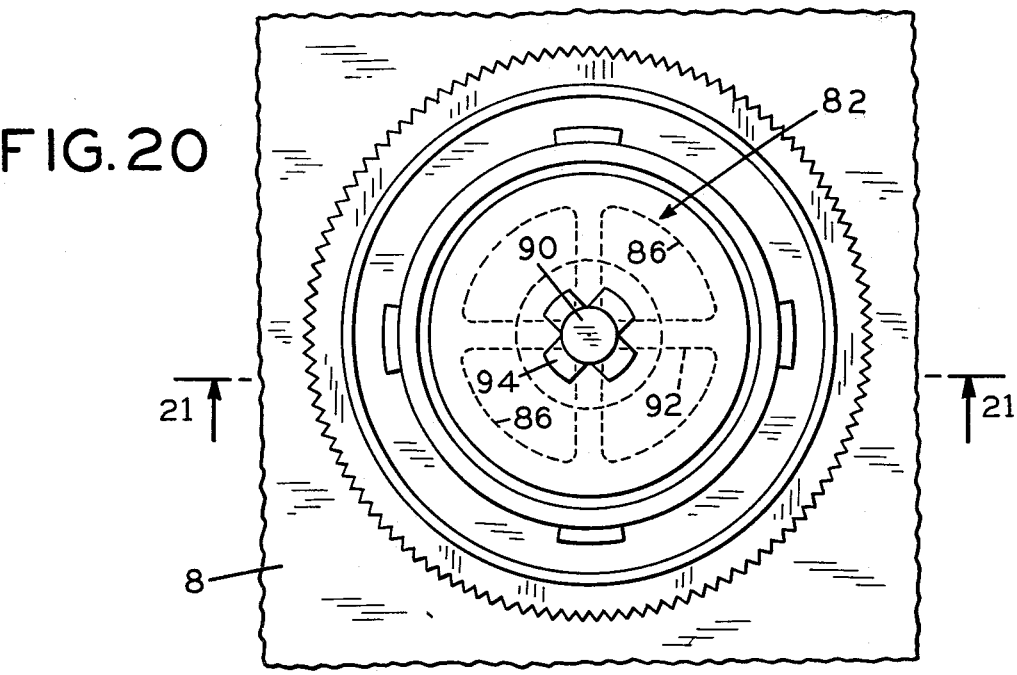
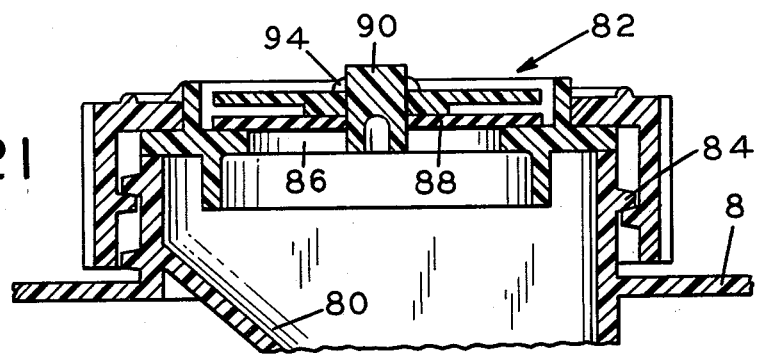
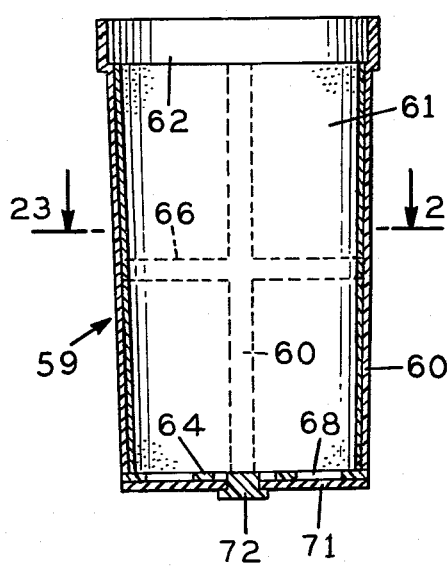
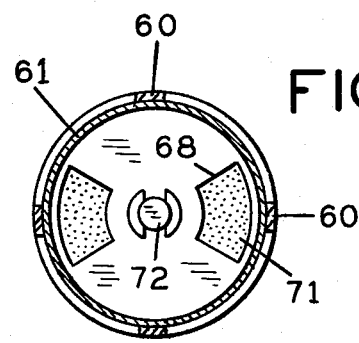
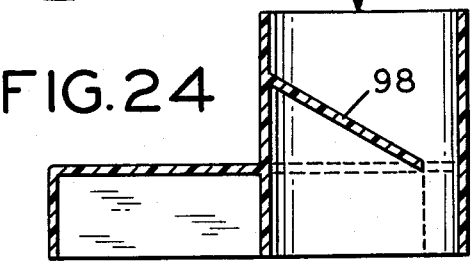

UNDERWATER DRAINAGE DEVICE

BACKGROUND OF INVENTION

It is well known in treating pneumothorax and other conditions of the pleural cavity that it is essential to remove excess fluids, blood, and gases, such as air, from the pleural space between the lung and the surrounding rib cage. Fluids may accumulate in the space between the lung and the chest wall as a result of surgery or from some other piercing of the rib cage, or from an illness. In such situations it is essential to the patient's survival that such fluids and/or gases be removed from the pleural cavity in order to maintain the lung in a fully expanded state and to restore pulmonary function.

There are know prior art devices and tehcniques for removing such fluids from the pleural cavity. These are known as the "one bottle", "two bottle" and "three bottle" systems.

The "one bottle" system consists of a single bottle with a connector adapted to be connected to the patient. The bottle contains a water seal and another opening which is an air vent.

The "two bottle" system consists of two bottles, the first being a collection bottle and water seal chamber attached to the patient and the second bottle being a suction control chamber. The first and second bottles are in fluid communication.

The prior art also includes what is known as the "three bottle" system. The prior art "three bottle" system utilizes a first or collection container in fluid communication with the patient and adapted to receive liquids and gases from the pleural cavity, a second container comprising a liquid seal which permits the evacuated gases to bubble out of the first or trap container and which prevents the flow of air back into the pleural cavity, and a third container which is a means of regulating vacuum or suction used to draw out the fluids and gases from the pleural cavity.

Thus in the "three bottle" system, one bottle serves as a trap container, a second bottle serves as a seal chamber and contains water to form that seal and the third bottle establishes the requisite negative pressure by being connected to a source of suction.

In the one, two and three bottle systems the water seal acts like a one-way valve, that is, it permits gases and liquid to be removed from the patient's pleural cavity but prevents the flow of gases back to the pleural cavity.

There are several disadvantages to the classical one, two and three bottle systems.

First, such systems have typically included glass containers or chambers with the resultant possible danger of breakage either during use or transport of the patient. Secondly, many such prior art systems employ corks and glass tubings with the possibility of leakage around the corks and glass tubings and breakage of the glass tubing either during use, assembly or disassembly. Of course, the two and three bottle systems greatly multiply the opportunity for such leakage and breakage due to the increased number of connections. Additionally, with some forms of the two and three bottle systems there is a danger of improper hookup to the patient even by skilled personnel.

Recently, some of the problems of breakage and leakage have been reduced by the use of a unitized plastic construction divided into a plurality of compartments or chambers which are constructed and arranged to perform the function of the three bottle systems. Such an arrangement is illustrated in U.S. Pat. Nos. 3,363,626, 3,363,627 and 3,559,647.

The unitized construction has the advantages of ease of transport and non-breakability.

There is a need, however, for an underwater drainage system which is reliable, relatively easy to manufacture, safe to operate, simple to understand, and not easily damaged. The underwater drainage system should be constructed so that the collection chamber can be easily emptied or samples taken therefrom for testing without disturbing the water seal or the manometer setting. Similarly, the water seal chamber should be capable of being filled accurately and expeditiously. The manometer chamber should be separable to permit ease in emptying or changing the level of liquid therein. The collection chamber, water seal chamber and manometer chamber should be in fluid communication by virtue of a manifold to which the collection and manometer chambers are removably attached.

BRIEF DESCRIPTION OF THE INVENTION

The present invention relates to a new and improved underwater drainage device which can be of the three bottle type. Thus, the underwater drainage device of the present invention includes a collection chamber adapted to be in fluid communication with the pleural cavity, a water seal chamber in fluid communication with the collection chamber and a manometer chamber. There is a manifold which maintains the chambers in fluid communication. The collection chamber is readily detachable from the manifold so that the collection chamber can be emptied or samples taken therefrom.

Similarly, the manometer chamber is readily detachable from the manifold so the level of liquid therein can easily be changed, i.e., raised or lowered without difficulty and without effecting the level of liquid in the collection or water seal chamber.

The manifold or horizontal conduit which provides fluid communication between the collection, water seal and manometer chambers also includes baffle means which prevents unwanted and undesirable fluid loss from one chamber to the adjacent chamber.

Another feature of the invention is an anti-reflux device positioned in the water seal chamber which inhibits the back-flow of the water seal liquid to the collection chamber. In the case of high negativity at the patient caused by coughing or the like there is a tendency of the liquid or water seal to be pulled toward the collection chamber. This, of course, could cause loss of water seal and would be undesirable for the patient.

With the anti-reflux device of this invention such a tendency is inhibited for a period of time sufficient that the period of high negativity passes. The anti-reflux device of the present invention includes a liquid permeable cylinder of controlled porosity which retards but does not stop the flow of liquid. When the period of high negativity ends the liquid can flow back to the water seal.

Other features of the invention include a floor stand which can be positioned generally parallel to the three chambers or perpendicular thereto, and easily accessible openings for ease of filling the water seal chamber and the manometer chamber. Additional features of the invention will be set forth in the detailed description of the invention.

The invention consists of the novel parts, constructions and improvements shown and described.

OBJECTS

With the foregoing in mind, it is an object of this invention to provide a new and improved underwater drainage device.

Another object of this invention is to provide a new and improved underwater drainage device including a collection, water seal and manometer chamber and an interconnecting manifold wherein the collection and manometer chambers are removable from the manifold.

Another object of this invention is to provide a new and improved underwater drainage device which provides increased accuracy in measurements.

A further object of this invention is to provide a new and improved underwater drainage device which is economical, easy to use and is safe in use.

Another object of this invention is to provide a new and improved underwater drainage device wherein the collection chamber is removable so as to permit emptying the collection chamber or taking samples therefrom for testing without affecting the water seal chamber or the manometer chamber.

A further object of this invention is to provide a new and improved underwater drainage device having an anti-reflux device in cooperative relationship with the water seal chamber which retards fluid flow towards the patient from the water seal chamber during periods of high negativity in the pleural cavity.

Another object of this invention is to provide a new and improved underwater drainage device having a stand giving increased stability to the underwater drainage device.

Another object of this invention is to provide a new and improved underwater drainage device having a suction chamber which is removable so that the liquid level may be changed thus changing the suction level to the desired value without affecting the collection chamber or the water seal chamber.

A still further object of this invention is to provide a new and improved underwater drainage device having a collection chamber with a plurality of calibrated subchambers giving increased accuracy in measuring patient drainage.

A still further object of this invention is to provide a new and improved underwater drainage device having means within the manometer chamber for decreasing agitation and noise therein.

Another object of this invention is to provide a new and improved underwater drainage device wherein the water seal chamber and the manometer chambers can be conveniently filled with liquid to the desired level.

A still further object of this invention is to provide a new and improved underwater drainage device having foot means for decreasing agitation and noise in the manometer chamber and for preventing spillage therefrom.

Another object of this invention is to provide a new and improved underwater drainage device having pressure relief means therein.

Additional objects and advantages of the invention will be set forth in the description which follows and in part will be obvious from the description, the objects and advantages being realized and obtained by means of the instrumentation, parts and apparatus particularly pointed out in the appended claims.

The accompanying drawings which are incorporated in and constitute part of this specification illustrate embodiments of the invention and together with the description serve to explain the principles of the invention.

OF THE DRAWINGS:

FIG. 1 Is an exploded drawing, of the invention showing various components of the underwater drainage device, before assembly.

FIG. 2 Is a front view of the upper portion of the invention.

FIG. 2A Is a front view of the lower portion of the invention.

FIG. 4 Is an end view of same, taken along Line 4—4 of FIG. 2.

FIG. 5 Is a vertical section taken through the upper portion of the invention, taken along line 5—5 of FIG. 3.

FIG. 5A Is a vertical section taken through the lower portion of the invention.

FIG. 6 Is a vertical section taken generally along line 6—6 of FIGS. 2, 5 and 8.

FIG. 12 Is a plan view of the neck portion of the collection chamber, showing the external locking threads.

FIG. 13 Is a front view of same.

FIG. 14 Is a diagrammatic development of the threads shown in FIGS. 13 and 14.

FIG. 15 Is a plan view of the mating locking threads shown in FIGS. 13, 14 and 15, these threads being molded in the manifold.

FIG. 20 Is a plan view of the pressure relief valve.

FIG. 21 Is a vertical section taken along line 21—21 of FIG. 20.

FIG. 22 Is a vertical section through the anti-reflux filter.

FIG. 23 Is a plan view in section taken along line 23—23 of FIG. 22.

FIG. 24 Is a vertical section taken along line 24—24 of FIGS. 3 and 5.

FIG. 25 Is a vertical sectional elevation of the foot base shown in the suction control chamber, taken along line 25—25 of FIG. 9.

FIG. 26 Is a plan view in section, taken along line 26—26 of FIG. 25.

DETAILED DESCRIPTION OF THE INVENTION

Figure 3:
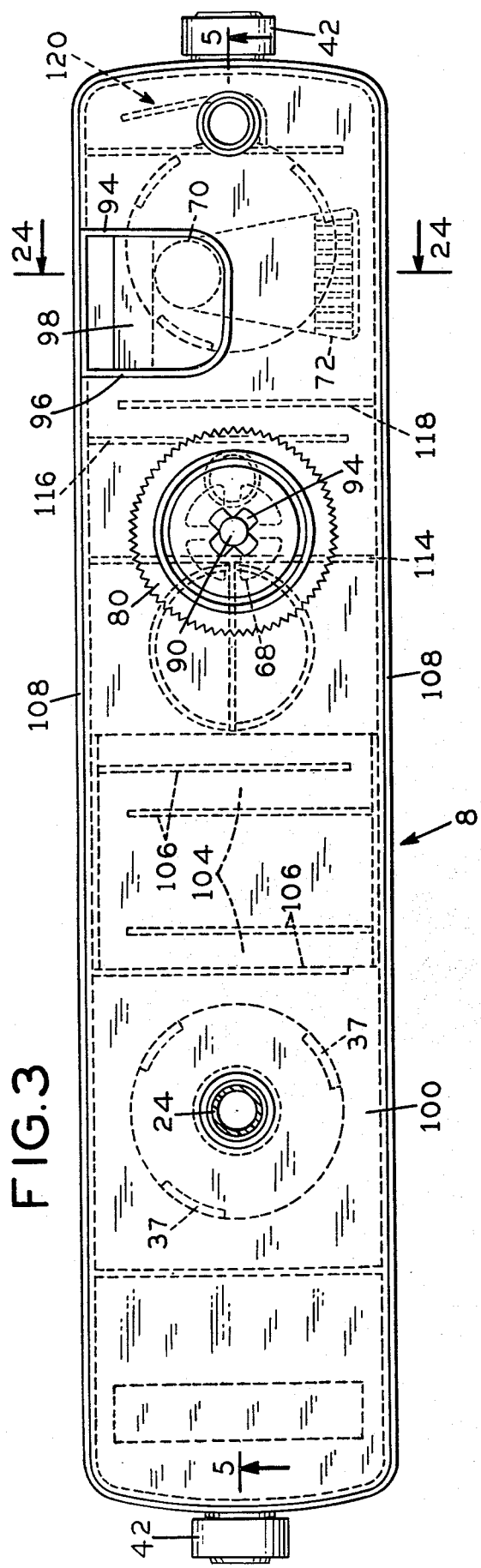
FIG. 3 Is a plan view of same.

A detailed description of the invention with specific reference to the drawings is set forth below.

Referring to FIG. 1 there is shown the main components of the invention; namely, the collection chamber 2, the water seal chamber 4, the manometer chamber 6, the manifold 8 and the stand 10. The manifold 8 is removably connected to the collection chamber 2, and the manometer chamber 6 and is attached in a fluid tight manner to the water seal chamber 4. The manifold 8 also provides the desired fluid communication between the collection, water seal and manometer chamber thus eliminating the need for hoses, conduits and the like frequently used in connection with underwater drainage devices.

The collection chamber 2 and the manometer chamber 6 are detachable from the manifold whereas the water seal chamber 4 is connected to the manifold. Preferably, the collection, water seal and manometer chambers and the manifold are made of a suitable plastic material such as polycarbonate and ABS so as to be easily formed as by molding and not susceptable to easy breakage in the event of rough treatment in transportation or usage.

The advantages of having the collection chamber easily removable from the manifold are that such an arrangement permits the collection chamber to be removed and emptied when desired without disturbing the contents of the water seal chamber or the manometer chamber and that removability of the collection chamber permits sampling such as for testing or analysis of the contents of the collection chambers.

By making the manometer chamber removable, it is a simple matter to reduce the level of liquid in the manometer, if desired, without disturbing either collection chamber or the water seal chamber. Thus, when it is desired to change the amount of suction this can be done quickly and expeditiously.

The invention includes a stand means 10 in which the collection, water seal and manometer chambers can be positioned to provide stability to the underwater drainage device when in operational use. As embodied, the stand means includes three seats 14, 16 and 18 (FIG. 10) for the respective chambers for maintaining the chambers in desired position when the stand is placed in parallel relation with the three chambers.

Figure 11:
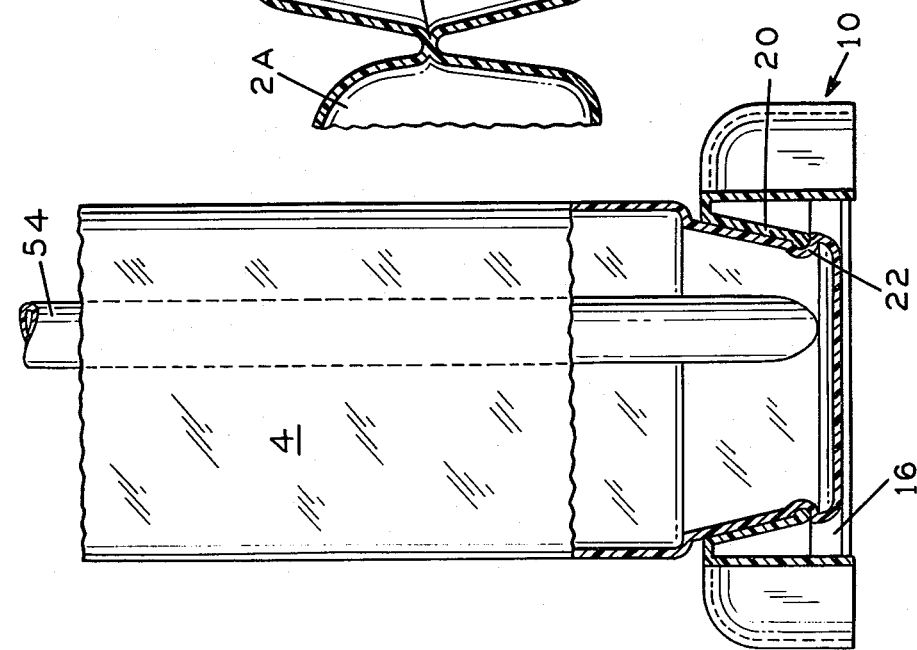
FIG. 11 Is a vertical section taken along line 11 of FIG. 9.
Figure 19:
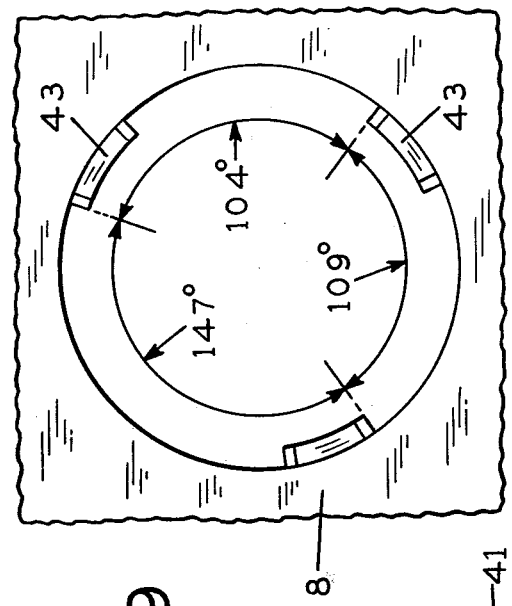
FIG. 19 Is a plan view of the mating locking threads shown in FIGS. 15, 17 and 18, these threads also being molded in the manifold.
Figure 16:
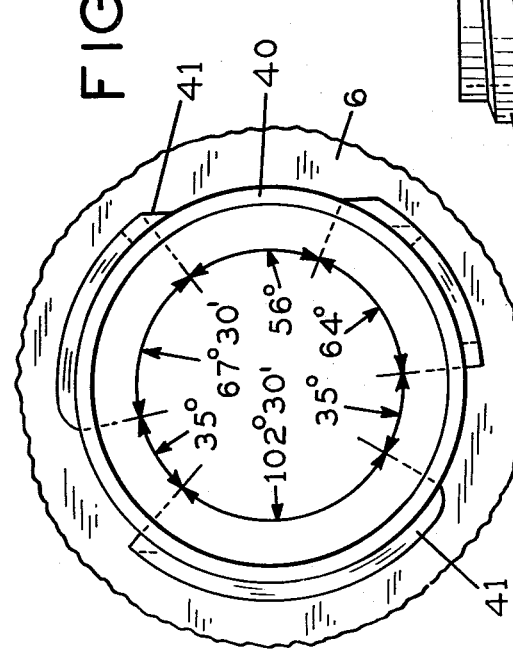
FIG. 16 Is a plan view of the neck portion of the suction control chamber, showing the external locking threads.
Figure 17:
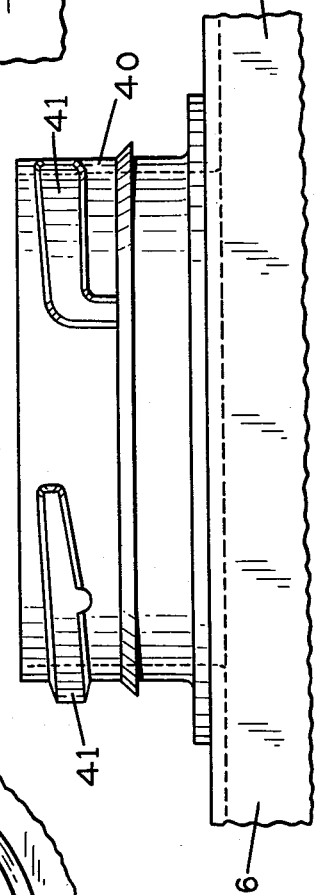
FIG. 17 Is a front view of the showing in FIG. 16.
Figure 18:
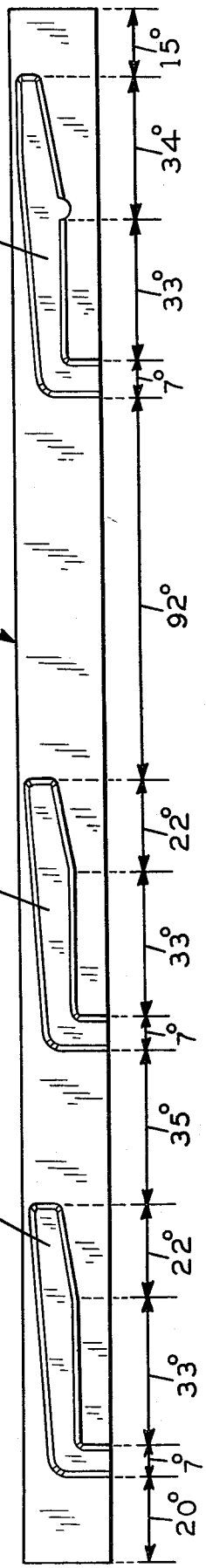
FIG. 18 Is a diagrammatic development of the threads shown in FIGS. 16 and 17.

The middle seat 16 of the stand includes flexible legs 20 (FIG. 11) adapted to engage a groove 22 in the wall of the water seal chamber in a snap-fit fashion.

Figure 10:
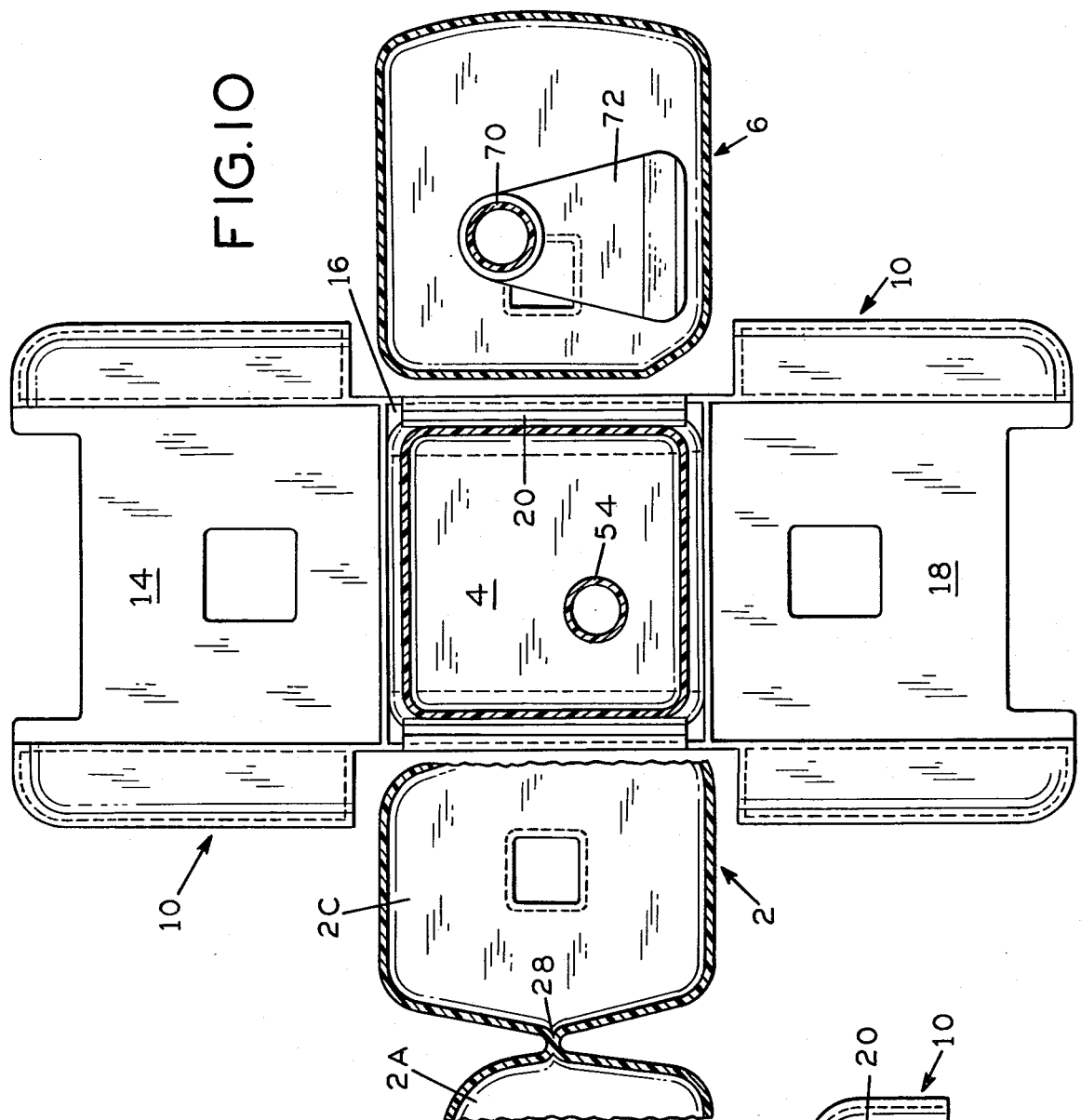
FIG. 10 Is a plan view similar to FIG. 9, showing the stand rotated 90° from the position shown in FIG. 9.

As shown in FIG. 10, the stand can be positioned in perpendicular position with respect to the line of chambers for additional stability. In this instance only the middle seat 16 is used to hold a chamber, namely, the water seal chamber. The other two seats serve as stabilizers.

The collection chamber 2 is in fluid communication with the pleural cavity by the drainage conduit 24 which includes an accordian like portion 26 so as to provide flexibility without kinking to the drainage conduit 24. The drainage tube chambered at 45° includes internal ridges 24' so that the fluid falls directly into the chamber. When in its assembled position, the drainage conduit 24 extends directly into the collection chamber through an opening in the manifold.

In order to provide increased accuracy to the collection chamber it is provided with walls 25 and 28 which with the outer walls divide the collection chamber into three compartments 2A, 2B and 2C. The dividing wall 25 is shorter than dividing wall 28 so that compartment 2A to which drainage conduit 24 leads fills first and gives great accuracy where there is relatively small amount of drainage. After compartment 2A is filled there will be spillover to compartment 2B and then to compartment 20. Each compartment has graduations 30 thereon so that the attending physician or nurse can determine at a glance the amount of drainage from the patient as can best be seen in FIGS. 1 and 2.

The collection chamber 2, as noted before, is detachably connected to the manifold 8. This is accomplished by a bayonet type connection illustrated in the drawings (FIG. 5). The bayonet type connection is constructed so that the collection chamber can only be connected to the manifold so as to be parallel with the water seal chamber. The bayonet connection includes ridges 33 in the neck 35 of the collection chamber adapted to engage lugs 37 on the manifold 8. The connection is made fluid tight by the gasket 38. By proper interrelation of the ridges 33 and the neck 35 it can be arranged, if desired, that the collection chamber will be connected to the manifold in the same position. For example, the ridges and grooves can be constructed and arranged so that the indicia markings thereon always face in the same direction as the indicia on the water seal chamber.

Similarly, as shown in FIGS. 16-19, there is bayonet type connection on the suction chamber neck 40 and the manifold 8 so that the suction or manometer chamber can only be connected to the manifold 8 so that it is parallel to the water seal chamber 4. In this instance there are ridges 41 on the neck of the suction chamber which are engagable with lugs 43 on the manifold 8. A gasket 45 provides a fluid tight connection. As in the case of the collection chamber the ridges and lugs can be constructed and arranged, if desired, so that the suction chamber can be removably attached to the manifold in only one position.

It is sometimes desirable to hang the underwater drainage device from the side of the bed or from some other object. For this purpose a pair of hooks 42 are positioned at each end of the manifold 8 (FIGS. 2, 4 and 5). The hooks have openings 44 so as to be rotatably connected to the trunnions 46 at each end of the manifold. In this way the hooks 42 can be rotated into and out of operating position.

In accordance with his invention an anti-reflux means is provided for retarding the flow of the liquid seal from the water seal chamber to the patient, in the event of a high degree of negativity occurring at the patient while the underwater drainage device is in use.

There are times when a high degree of negativity will occur in the patient's pleural cavity such as when the patient coughs or the like. When this occurs there is a tendency for the liquid in the water seal chamber to go towards the patient. Should this occur it would be highly undesirable and could cause loss of water seal protection.

The anti-reflux means 50 (FIGS. 5, 22 & 23) in accordance with this invention is located within the water seal chamber and includes a tubular portion 52 in telescoping engagement with the water seal tube 54 which extends down into the water seal. The tubular portion is expanded into an enlarged open ended cylinder portion 56. The enlarged open ended cylinder 56 is connected to or is an extension of the manifold 8 and has a ledge 58 adjacent the open end of the cylinder for positioning the anti-reflux member within the water seal chamber.

In accordance with this invention means is provided for positioning within the cylindrical portion means for retarding the flow of liquid to the patient in the event of high negativity at the patient such as can be caused by coughing.

As embodied, this means includes a frame member 59 having a plurally, preferably four, vertical struts 60 joined together by top 62 and bottom 64 and center 66 cylindrical supports. The diameter of the upper or top support 62 is larger than the diameter of the center and bottom support. The lower surface of the top cylindrical support 62 is adapted to rest on the ledge 58 at the top of the open cylinder 56. By virtue of the fact that upper support 62 is larger in diameter than the lower 64 and middle 66 supports the vertical walls are spaced a short distance from the inside surface of the enlarged cylinder 56.

Attached to the inner surfaces of the frame member 59 is a thin cylinder 61 of membranous material made of a suitable hydrophobic material.

While this thin cylinder 61 of membranous material is made of hydrophobic material, it is sufficiently porous to allow liquid, i.e. water, to pass through when there is a high degree of negativity in the pleural cavity of the patient.

The bottom wall 64 has openings 68 therein. A flexible rubber gasket member 71 is attached to the bottom wall 64 by a rivet 72 or the like. Except for the rivet 72 the gasket is otherwise not attached to the bottom wall 64.

In use, the anti-reflux device operates as follows:

When there is a period of high negativity at the patient, liquid from the water seal chamber will rise and will enter the space in the cylinder below the flexible gasket or diaphram 71. At this time, the rubber gasket 71 closes the openings 68 in the bottom support surface. As the negativity continues the liquid will rise in the space between the cylindrical member 56 and the hydrophobic material 61. Eventually, if the high negativity continued, the liquid would fill the cylinder and would be drawn towards the patient, since the hydrophobic material retards but does not stop the flow of liquid.

However, the period of time of high negativity is relatively short, such caused by a cough or the like and the retarding of the liquid flow is sufficient so that fluid is not likely to be directed towards the patient.

When the period of high negativity in the pleural cavity ends, the liquid within the cylinder formed by the hydrophobic material will retreat. At this time, the flexible gasket 71 will move away from the openings 68 in the bottom support plate so that the liquid can rush back into the seal chamber.

The manometer chamber 6 is, of course, normally subjected to a negative pressure since it is connected to a source of vacuum. As can be seen, there is a tube 70 which extends from the fill port 96 to the bottom of the manometer chamber.

Because of the vacuum applied by the vacuum source, there can be a substantial amount of bubbling from the tube 70 which can be disturbing and noisy.

In accordance with this invention means is provided for reducing the amount of bubbling in the suction chamber.

As embodied, this means includes a foot member 72 which is attached to the tube 70 in any convenient manner. The foot member is enlarged and at its terminal or toe end includes a plurality of relatively small openings 74 (FIG. 26). The foot is attached to the tube 70 so that the air bubbles emanating from the foot through the openings 74 hit the front wall of the device and the bubbles will follow a circular path to minimize splashing within the chamber. This circular pattern also helps prevent fluid from entering the suction line.

The manifold 80 provides for desired fluid communication between the chambers, means for directing water to the water seal chamber and the suction chamber and includes means for preventing spillage in the event the device is accidentally placed in the wrong position.

As embodied, and shown in FIGS. 20-21, the manifold includes a water seal fill passageway 80 which is in the form of an offset funnel. A pressure relief valve 82 is provided so as to prevent build up of positive pressure in the unit. The pressure relief valve is contained in the water seal fill cap. The pressure relief valve includes a plurality of openings 86 which are normally closed by a thin rubber membrane 88 which is attached in any convenient fashion to the post 90 which is centered by the struts 92 extending between the openings 86. A plurality of wedge-shaped elements 94 extend downwardly from the top of center post 90.

In use, in the event of a pressure build-up within the water seal chamber, such pressure will be relieved by pushing the rubber membrane away from the openings 86.

As shown in FIG. 5, there is a filling means for the suction chamber consisting of a raised rectangular portion 96 (FIG. 24) which provides for easy access to the suction chamber. Within the rectangular portion 96 is a guide member 98 which is slanted downwardly towards the suction chamber. The filling means provides for easy access to the suction chamber and the slanted member permits ease of filling and at the same time assists in preventing spillage as a result of tipping the device or turbulence within the manometer chamber.

Figure 7:
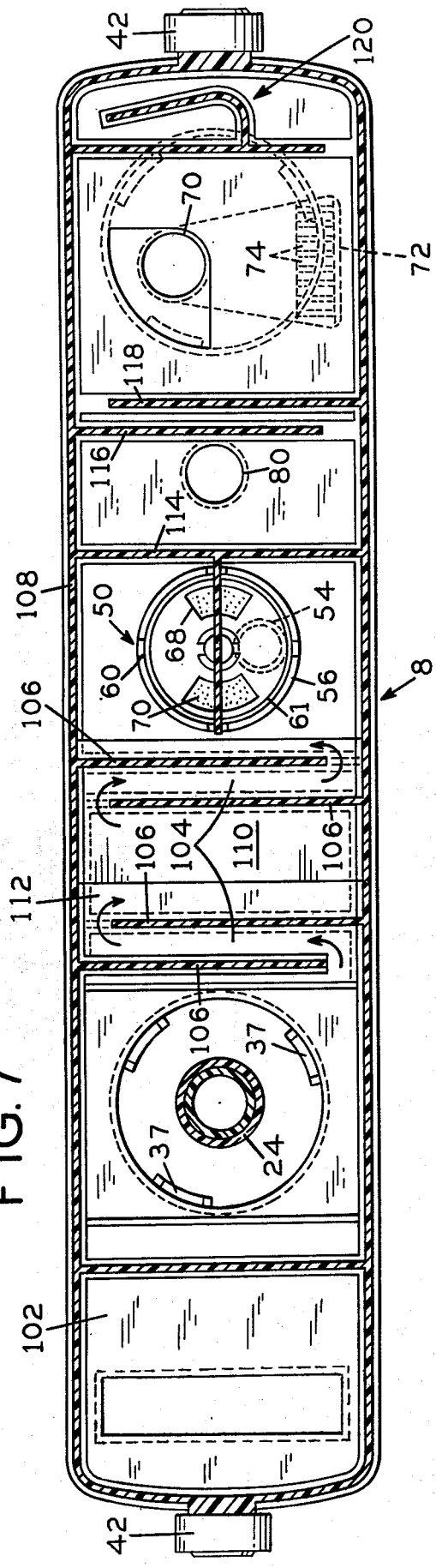
FIG. 7 Is a plan view in section taken along line 7—7 of FIG. 5.
Figure 8:
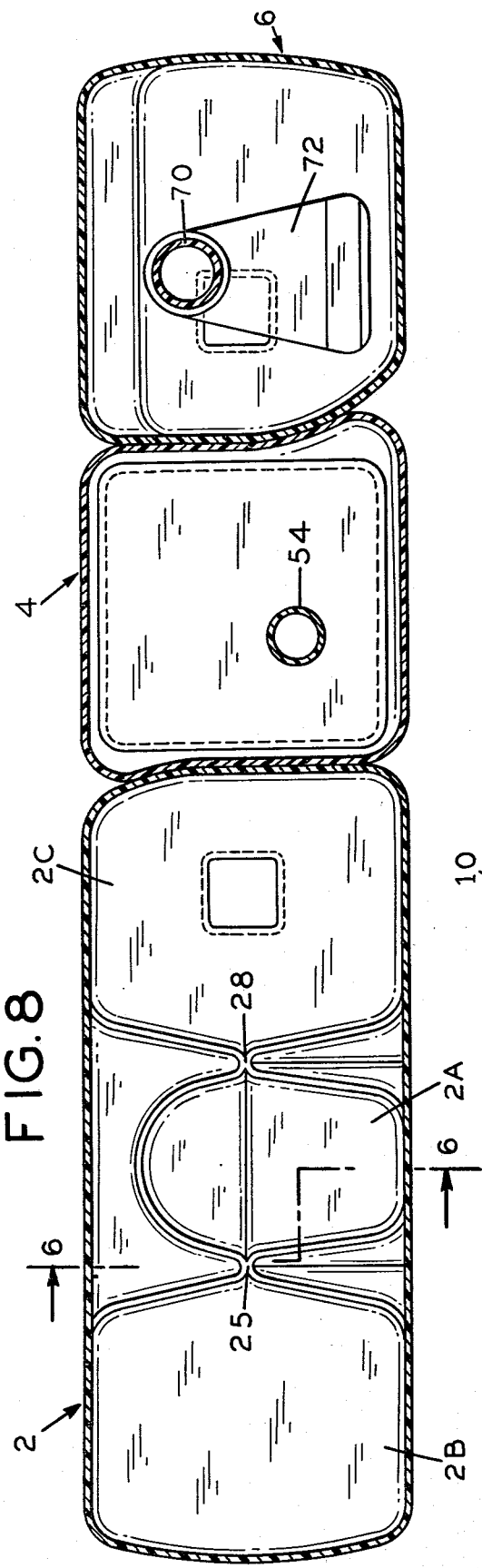
FIG. 8 Is a plan view in section taken generally along line 8—8 of FIG. 5.
Figure 9:
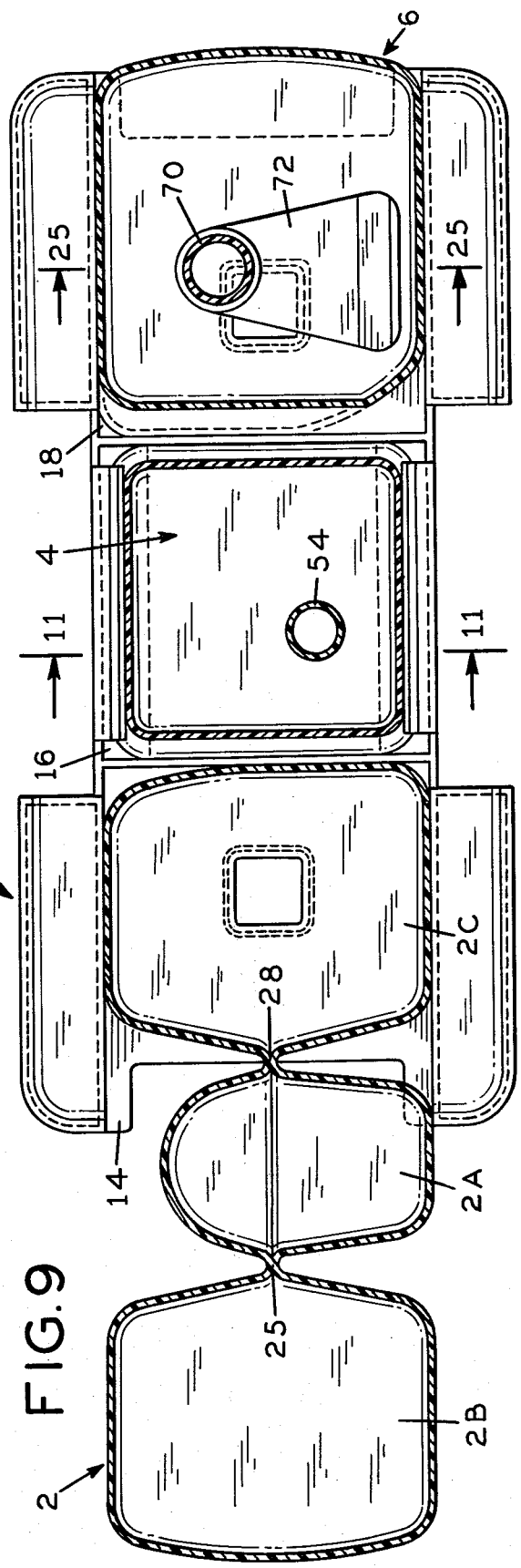
FIG. 9 Is a plan view in section, taken along line 9—9 of FIG. 5, showing the stand in parallel position to the invention.

Referring to FIGS. 3, 5 and 7, the manifold is shown in detail. Essentially the manifold consists of separate upper 100 and lower 102 halves which are joined together in a fluid tight manner in any desired fashion.

As shown in FIG. 7, there is a sinuous passageway 104 between the entrance to the collection chamber and the entrance to the water seal chamber which provides for fluid communication but deters liquid, i.e., water flow between the collection and the water seal chambers in the event the unit is accidentally tipped. The passageway 104 consists of four parallel baffles 106 wich extend only partially between the sides 108 of the manifold in any alternate fashion so there is a sinuous passageway. The sinuous passageway assists in preventing liquid flow between the collection chamber and the water seal chamber in the case of accidental tipping. Positioned between the inner pair of baffles 106 are slanted bottom portions 110 and 112 which extend to a height sufficient to deter fluid communication between the water seal chamber so as to deter liquid flow between the water seal chamber and the collection chamber. The slanted bottom portions 110 and 112 cause the water to flow downwardly.

The manifold member also includes means for preventing liquid, i.e., water flow between the manometer chamber and the water seal chamber.

As can be seen in FIG. 7, there is a solid wall 114 which is a barrier between the patient side of the device and the suction side of the device.

Intermediate the filling funnel 80 for the water seal chamber and the manometer chamber are baffle walls 116 and 118. As can be seen baffle wall 116 extends towards but not to one of the side walls 108 whereas baffle wall 118 extends towards but not to the other side wall 108. There is thus formed a sinuous path between the water seal chamber which deters liquid flow between the chambers. The baffle 120 (FIG. 7) is a barrier which prevents water flow to the suction pump (not shown) through the suction line.

What is claimed is:

1. An underwater drainage device for removing liquids and gases from the pleural cavity of a patient comprising:
    (a) a collection chamber having a flexible tube in fluid communication with the pleural cavity of a patient so that the fluid from the patient will be directed to said collection chamber;
    (b) a liquid seal chamber having a predetermined amount of liquid therein;
    (c) a suction chamber adapted to be connected to a source of suction and having a level of liquid therein;
    (d) an enclosed manifold member having side walls, connected to and forming a passageway between said collection chamber;
    (e) means on said manifold member for providing fluid communication between said collection chamber, said water seal chamber and said suction chamber so that fluid and gases from the patient will pass to said collection chamber, gases can pass from the collection chamber to the water seal chamber and the suction chamber;
    (f) means for removably interconnecting said collection chamber to said manifold so as to permit removal of liquid from the collection chamber without disturbing the contents of the water seal chamber or the suction chamber;
    (g) means for removably interconnecting said suction chamber and said manifold so as to permit changing of the level of liquid therein; and
    (h) baffle means spaced along and extending from said side walls into the passageway in said manifold member providing a sinuous path between said chambers to permit gases to pass between said chambers while deterring liquid from passing between said chambers.

2. An underwater drainage device as defined in claim 1 wherein said means for interconnecting said collection chamber and said manifold consist of a bayonet connection consisting of cooperating ridges and lugs.

3. An underwater drainage device as defined in claim 1 wherein said means for interconnecting said suction chamber and said manifold consists of a bayonet connection consisting of cooperating ridges and lugs.

4. An underwater drainage device as defined in claim 2 wherein said lugs are on said manifold and said ridges are on said collection chamber.

5. An underwater drainage device as defined in claim 3 wherein said lugs are on said manifold and said ridges are on said suction chamber.

6. An underwater drainage device as defined in claim 1 wherein said manifold, said collection chamber, said seal chamber and said suction chamber are made of plastic.

7. An underwater drainage device as defined in claim 1 having a positive pressure relief valve operatively associated with said water seal chamber, said pressure relief valve including a plurality of openings which are closed by a rubber membrane.

8. An underwater drainage device as defined in claim 1 having stand means for positioning the device on a flat surface, said stand means having at least two positions.

9. An underwater drainage device as defined in claim 1 having hook means for hanging said device adjacent a patient.

10. An underwater drainage device as defined in claim 1 having a drainage tube extending from the collection chamber to a patient and means on said drainage tube to prevent kinking of said drainage tube.

11. An underwater drainage device as defined in claim 1 wherein said manifold includes barrier means for preventing liquid flow between the collection chamber and the water seal chamber.

12. An underwater drainage device as defined in claim 11 having a barrier separating the collection chamber from the suction chamber.

13. An underwater drainage device as defined in claim 1 having a suction line in said suction chamber and barrier means for preventing liquid return flow through the suction line.

14. An underwater drainage device as defined in claim 1 having foot means within said suction chamber for reducing liquid agitation.

15. In an underwater drainage device having a collection chamber adapted to be connected in fluid communication with the pleural cavity of a patient, a liquid seal chamber in fluid communication with said collection chamber and a suction chamber in fluid communication with said seal chamber; retarding means comprising:
    (a) a water seal tube extending into said liquid seal chamber in fluid communication with said collection chamber;
    (b) an open ended cylinder connected to said water seal tube;
    (c) a liquid retarding frame means having a plurality of vertical struts interconnected by a plurality of circular support means adapted to position within said open ended cylinder;
    (d) a membranous material connected to said frame so as to retard the flow of liquid from the water seal chamber towards said collection chamber.

16. An underwater drainage device as defined in claim 15 wherein said membranous material is hydrophobic.

17. A liquid retarding means for use in an underwater drainage device having a collection chamber adapted to be in fluid communication with the pleural cavity of a patient and a water seal chamber having a predetermined level of liquid therein comprising:
    (a) a water seal tube extending into said water seal chamber, and in fluid communication with said collection chamber;
    (b) an open ended cylinder in engagement with said water seal tube, said open ended cylinder including an enlarged diameter portion,
    (c) a liquid flow retarding frame means positioned within said enlarged diameter portion,
    (d) a membranous material connected to said frame so that there is a space between said membranous material and the wall of said enlarged diameter portion,
    (e) said membranous material being positioned so as to retard the flow of liquid from the water seal chamber when there is a high negativity in the pleural cavity; and (f) means for permitting liquid to return to said water seal chamber when the period of high negativity ends.

18. An underwater drainage device as defined in claim 17 wherein there is a flexible gasket at the bottom of said cylindrical frame which permits liquid flow in one direction.

19. An underwater drainage device as defined in claim 17 having barrier means for preventing liquid flow between said water seal chamber and said collection chamber and barrier means for preventing return liquid flow through said suction line.

20. An underwater drainage device as defined in claim 19 having means for maintaining said device in an operative position.

21. An underwater drainage device as defined in claim 20 wherein said means for maintaining consists of a stand.

22. An underwater drainage device as defined in claim 20 wherein said means for maintaining consists of hooks.

23. An underwater drainage device for removing liquids and gases from the pleural cavity of a patient comprising:
(a) a collection chamber having a flexible tube in fluid communication with the pleural cavity of a patient so that fluid from the patient will be directed to said collection chamber;
(b) a liquid seal chamber having a pre-determined amount of liquid therein;
(c) a suction chamber adapted to be connected to a source of suction and having a level of liquid therein;
(d) a manifold member connected to said collection chamber, said water seal chamber and said suction chamber;
(e) means on said manifold member for providing fluid communication between said collectin chamber, said water seal chamber and said suction chamber so that fluid and gases from the patient will pass to said collection chamber, gases can pass from the collection chamber to the water seal chamber and the suction chamber;
(f) means for removably interconnecting said collection chamber to said manifold so as to permit removal of liquid from the collection chamber without disturbing the contents of the water seal chamber or the suction chamber;
(g) means for removably interconnecting said suction chamber and said manifold so as to permit changing of the level of liquid therein;
(h) a liquid retarding means in said water seal chamber for retarding liquid flow from said seal chamber to said collection chamber; and
(i) said retarding means including an open ended cylindrical frame positioned within said seal chamber in fluid communication with said collection chamber, said frame member supporting a hydrophobic membraneous member which retards fluid flow from said water seal chamber to said collection chamber.

24. An underwater drainage device for removing liquids and gases from the pleural cavity of a patient comprising:
(a) a collection chamber having a flexible tube in fluid communication with the pleural cavity of a patient so that fluid from the patient will be directed to said collection chamber;
(b) a liquid seal chamber having a pre-determined amount of liquid therein;
(c) a suction chamber adapted to be connected to a source of suction and having a level of liquid therein;
(d) a manifold member connected to said collection chamber, said water seal chamber and said suction chamber;
(e) means on said manifold member for providing fluid communication between said collection chamber, said water seal chamber and said suction chamber so that fluid and gases from the patient will pass to said collection chamber, gases can pass from the collection chamber to the water seal chamber and the suction chamber;
(f) means for removably interconnecting said collection chamber to said manifold so as to permit removal of liquid from the collection chamber without disturbing the contents of the water seal chamber or the suction chamber;
(g) means for removably interconnecting said suction chamber and said manifold so as to permit changing of the level of liquid therein;
(h) a positive pressure relief valve operatively associated with said water seal chamber; and
(i) an offset funnel adapted to be used to add liquid to said water seal chamber wherein a pressure relief valve is operatively associated with said offset funnel.

25. An underwater drainage device for removing liquids and gases from the pleural cavity of a patient comprising:
(a) a collection chamber having a flexible tube in fluid communication with the pleural cavity of a patient so that fluid from the patient will be directed to said collection chamber;
(b) a liquid seal chamber having a pre-determined amount of liquid therein;
(c) a suction chamber adapted to be connected to a source of suction and having a level of liquid therein;
(d) a manifold member connected to said collection chamber, said water seal chamber and said suction chamber;
(e) means on said manifold member for providing fluid communication between said collection chamber, said water seal chamber and said suction chamber so that fluid and gases from the patient will pass to said collection chamber, gases can pass from the collection chamber to the water seal chamber and the suction chamber;
(f) means for removably interconnecting said collection chamber to said manifold so as to permit removal of liquid from the collection chamber without disturbing the contents of the water seal chamber or the suction chamber;
(g) means for removably interconnecting said suction chamber and said manifold so as to permit changing of the level of liquid therein;
(h) a positive pressure relief valve operatively associated with said water seal chamber, said pressure relief valve including a plurality of openings which are closed by a rubber membrane.

26. An underwater drainage device for removing liquids and gases from the pleural cavity of a patient comprising:
(a) a collection chamber having a flexible tube in fluid communication with the pleural cavity of a patient so that fluid from the patient will be directed to said collection chamber;
(b) a liquid seal chamber having a pre-determined amount of liquid therein;
(c) a suction chamber adapted to be connected to a source of suction and having a level of liquid therein;
(d) a manifold member connected to said collection chamber, said water seal chamber and said suction chamber;
(e) means on said manifold member for providing fluid communication between said collection chamber, said water seal chamber and said suction chamber so that fluid and gases from the patient will pass to said collection chamber, gases can pass from the collectin chamber to the water seal chamber and the suction chamber;
(f) means for removably interconnecting said collection chamber to said manifold so as to permit removal of liquid from the collection chamber without disturbing the contents of the water seal chamber or the collection chamber;
(g) means for removably interconnecting said suction chamber and said manifold so as to permit changing of the level of liquid therein;
(h) liquid retarding means in said water seal chamber for retarding the flow of liquid from said water seal chamber to said collection chamber in the event of high negativity in the patient's pleural cavity;
(i) means cooperating with said liquid retarding means for permitting liquid within liquid retarding means to return to said water seal chamber when the period of high negativity in the patient's pleural cavity ends; and
(j) foot means in said suction chamber for reducing agitation therein, said foot means including a plurality of side-by-side openings therein.

27. An underwater drainage device for removing liquids and gases from the pleural cavity of a patient comprising:
(a) a collection chamber having a flexible tube in fluid communication with the pleural cavity of a patient so that fluid from the patient will be directed to said collection chamber;
(b) a liquid seal chamber having a pre-determined amount of liquid therein;
(c) a suction chamber adapted to be connected to a source of suction and having a level of liquid therein;
(d) a manifold member connected to said collection chamber, said water seal chamber and said suction chamber;
(e) means on said manifold member for providing fluid communication between said collection chamber, said water seal chamber and said suction chamber so that fluid and gases from the patient will pass to said collection chamber; gases can pass from the collection chamber to the water seal chamber and the suction chamber;
(f) means for removably interconnecting said collection chamber to said manifold so as to permit removal of liquid from the collection chamber without disturbing the contents of the water seal chamber or the collection chamber;
(g) means for removably interconnecting said suction chamber and said manifold so as to permit changing of the level of liquid therein;
(h) liquid retarding means in said water seal chamber for retarding the flow of liquid from said water seal chamber to said collection chamber in the event of high negativity in the patient's pleural cavity;
(i) means cooperating with said liquid retarding means for permitting liquid within liquid retarding means to return to said water seal chamber when the period of high negativity in the patient's pleural cavity ends; and
(j) said collection chamber tube includes internal ridges and a chamfered end so that fluid drains directly into said center compartment of the collection chamber.

28. In an underwater drainage device adapted to be connected in fluid communication with the pleural cavity of a patient, said underwater device including a plurality of chambers at least one of which receives gases and liquids from the pleural cavity of a patient, an anti-spill means comprising:
(a) an enclosed manifold member having side walls and interconnecting said chambers;
(b) a passage in said manifold providing communication between said chambers;
(c) baffle means spaced along and extending from said side walls into said passageway;
(d) said baffle means being constructed and arranged in said passageway so that there is a sinuous path between said chambers which permits gas to flow between said chambers but prevents liquid from flowing between said chambers.

* * * * *